United States Patent [19]

Dunski

[11] Patent Number: 4,772,651

[45] Date of Patent: Sep. 20, 1988

[54] POLYOL CARBOXYALKYLTHIOALKANOESTER-PHENOL COMPOUNDS AND ORGANIC MATERIALS STABILIZED THEREWITH

[75] Inventor: Neil Dunski, Creve Coeur, Mo.

[73] Assignee: Mallinckrodt, Inc., St. Louis, Mo.

[21] Appl. No.: 67,751

[22] Filed: Jun. 29, 1987

[51] Int. Cl.$^4$ ............... C08K 5/36; C07C 149/273
[52] U.S. Cl. .................. 524/289; 252/48.6; 260/398.5; 560/15
[58] Field of Search ............ 524/289; 560/15; 252/48.6; 260/398.5

[56] References Cited

U.S. PATENT DOCUMENTS 3,285,855  11/1966  Dexter et al. ............ 524/291
3,546,272  12/1970  Braus et al. ............. 524/289
4,633,008  12/1986  Oonishi et al. ........... 560/15

Primary Examiner—Veronica P. Hoke
Attorney, Agent, or Firm—R. J. Klostermann; L. N. Goodwin; Veo Peoples

[57] ABSTRACT

Polyol carboxyalkylthioalkanoesterphenol compounds useful in the stabilization of organic materials normally susceptible to oxidative degradation are prepared by reaction of an appropriate polythio, which is a selected tetra-(mercapto alkanoic acid) ester of pentaerythritol or a selected tri-(mercapto alkanoic acid) ester of a selected 1, 1, 1-trimethylolalkane, with an appropriate alkenyl compound, which is a selected 4-hydroxy-(mono- or di-alkyl)phenylalkylalkenoate. In a preferred embodiment, the compound is pentaerythritol tetrakis [3,5-di-tert-butyl-4-hydroxyphenyl-(3-propyl)oxycarbonylethylthiopropionate].

17 Claims, No Drawings

POLYOL CARBOXYALKYLTHIOALKANOESTERPHENOL COMPOUNDS AND ORGANIC MATERIALS STABILIZED THEREWITH

This invention relates to polyol carboxyalkylthioalkanoesterphenol compounds useful in the stabilization of organic materials normally susceptible to oxidative degradation, a process for preparing the compounds and organic material stabilized with the compounds.

Numerous compounds, including various sterically hindered phenol derivatives, have been proposed for stabilizing organic materials, such as organic polymers, against oxidative and thermal degradation.

Knell et al, U.S. Pat. No. 3,679,744, discloses thiodialkanoamidophenol compounds (more specifically designated as N,N'-bis(alkylhydroxyphenyl)thiaalkanedicarboxamides) obtained by a procedure involving the reaction of a selected alkylaminophenol with a thiodialkanoyl chloride. According to the patent, these monosulfur compounds are useful as stabilizers of organic materials which are subject to oxidative deterioration. Poly-alpha-olefins such as polyethylene, polypropylene, polybutylene, polyisoprene and copolymers thereof are included among the organic materials set forth in the patent. One such monosulfur compound, disclosed in Example I thereof is N,N'-bis(3',5'-di-t-butyl-4'-hydroxyphenyl)-2-thiapropane-1,3-dicarboxamide.

Huber-Emden et al, U.S. Pat. No. 3,927,091, discloses thio carboxylic acid amides wherein the amido nitrogen is bridged through a methylene group to a 3,5-di-tert-butyl-4-hydroxyphenol group for stabilizing organic materials sensitive to oxidations.

Nakahara et al, U.S. Pat. No. 4,226,991, discloses a process for preparing a polyhydric alcohol 3-alkylthiopropionate polyolefin resin stabilizer. One such compound disclosed therein is pentaerythritol tetrakis (3-n-octylthiopropionate).

Homberg, U.S. Pat. No. 3,144,422, discloses esters of thiocarboxylic acids and stabilization of polymers with such esters. Compounds specifically disclosed therein include pentaerythritol tetra (beta-mercaptopropionate) and 1,1,1-trimethylolethane tri (beta-mercaptopropionate).

Beears, U.S. Pat. No. 3,742,032 discloses N,N'-alkylene-bis[beta-(alkylcarboxyalkylthio) propionamides] as stabilizers for polyolefins, particularly polyethylene and polypropylene. One such compound disclosed therein is N,N'-methylene-bis[beta-(n-dodecyl-2-carboxyethylthio)propionamide].

However, heretofore known compounds, such as the compounds set forth above, have not been entirely satisfactory for stabilizing organic materials, such as polyolefins (e.g., polyethylene and polypropylene), against oxidative and thermal degradation. Accordingly, there is a substantial need in the art for new compounds having the capability of stabilizing organic materials such as polyethylene and polypropylene against such degradation.

Dunski' U.S. Pat. No. 4,634,728 discloses polyol carboxyalkylthioalkanoamidophenol compounds and organic materials stabilized therewith. It has now been found that the hereinafter described polyol carboxyalkylthioalkanoesterphenol compounds have stabilizing capabilities. Such compounds are hereinafter sometimes referred to as polyol AB compounds or terms of similar import.

DESCRIPTION OF THE INVENTION

Generally stated, the present invention provides polyol AB compounds which may be represented by Formula I below:

Where Y is a monovalent group represented by Formula II below:

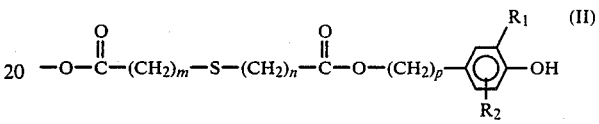

wherein $R_1$ is an alkyl group containing from one to eight carbon atoms or a cycloalkyl group containing from five to 12 carbons atoms; $R_2$ is hydrogen, an alkyl group containing from one to 8 carbon atoms or a cycloalkyl group containing from 5 to 12 carbon atoms; m is a selected integer from 1 to about 10, and n is a selected integer from 1 to about 14, p is a selected integer from to 1 about 8, preferably 3; and Z is $-CH_2Y$ or an alkyl group containing from one to about 8 carbon atoms; and X is Y or $-OH$. It is preferred that X is Y.

In still another aspect of this invention, there are provided organic compositions of matter stabilized against thermal-oxidative degradation, which comprise an organic material and a stabilizing amount of the compound of Formula I.

DETAIL DESCRIPTION OF THE INVENTION AND OF THE MANNER AND PROCESS OF MAKING AND USING IT

In the compounds of Formula II above where $R_2$ is other than hydrogen, in general each $R_2$ substituent is preferably located ortho to the hydroxyl group on its respective benzene ring, but may be in the meta position.

Suitable alkyl groups from which $R_1$ and $R_2$ may be selected include methyl, ethyl, propyl, isopropyl, butyl, amyl, hexyl, octyl, and the like. Included also are tertiary alkyl groups, such as t-butyl, t-amyl, t-octyl, and the like. Suitable cycloalkyl groups from which $R_1$ and $R_2$ may be selected include cyclopentyl, cyclohexyl, cyclooctyl, cyclododecyl, and the like. Preferably, $R_1$ and $R_2$ are t-butyl groups, with both $R_2$ groups located in their ortho positions. The number of $CH_2$ groups in the compounds is preferably such that each of m and n is 2 and each p is 3 in Formula II above.

The polyol AB compounds of this invention include, for example:
(a) Pentaerythritol tetrakis[3,5-di-tert-butyl-4-hydroxyphenyl-(3-propyl)oxycarbonylethylthiopropionate].
(b) Pentaerythritol tetrakis[3,5-di-tert-butyl-4-hydroxyphenyl-(3-propyl)oxycarbonylethylthioacetate].
(c) 1,1,1-trimethylolethane tris[3,5-di-tertbutyl-4-hydroxyphenyl-(3-propyl)oxycarbonylethylthiopropionate].

(d) 1,1,1-trimethylolpropane tris[3,5-di-tert-butyl-4-hydroxyphenyl-(3-propyl)oxycarbonylethylthioacetate].

Preferred compounds of this invention are compounds (a) and (c). Compound (a) above is most preferred and corresponds to Formula I above where Z is —CH₂Y, X is Y, and Y is represented by Formula III below:

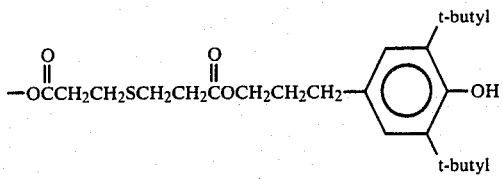

The polyol AB compounds of this invention can be prepared by reaction of polythiols with alkenes. The reaction is carried out by reacting an appropriate polythiol, i.e.—a selected tetra-[mercapto ($C_2$-$C_{11}$) alkanoic acid] ester of pentaerythritol, e.g., pentaerythritol tetra(3-mercaptopropionate) or pentaerythritol tetra(mercaptoacetate), or a selected tri-[mercapto ($C_2$-$C_{11}$)alkanoic acid] ester of a selected 1,1,1-trimethylolalkane, e.g., 1,1,1 trimethylolethane tri(3-mercaptopropionate) or 1,1,1-trimethylolethane tri(mercaptoacetate), with an appropriate alkenyl compound, i.e. a selected 4-hydroxy-(mono- or di-alkyl)phenyl alkyl alkenoate e.g. 4-hydroxy-3,5-di-tert-butyl-(3-propyl)acrylate. There should be used at least one gram-mole of the alkenyl compound per gram-equivalent of available thiol groups of the polythiol, i.e., at least 4 moles of the alkenyl compound per mole of tetra-thiol ester of pentaerythritol and at least 3 moles of the alkenyl compound per mole of 1,1,1-trimethylolalkane.

The reaction is carried out in a solution containing the reactants and at least a solubilizing amount of an inert solvent for at least one, and preferably both, of the reactants and a basic catalyst. Chloroform is preferred as the solvent. When n in Formula II is 2, the catalyst can be an alkali metal alkoxide such as sodium methoxide or quarternary ammonium hydroxide such as sodium methoxide or quarternary ammonium hydroxide such as trimethylbenzyl ammonium hydroxide (preferred), which is commercially available under the trademark Triton B (Rohm & Haas Co.). When n in Formula II is 3 or more, a free radical generator such as a peroxide or an azonitrile, (preferably azobisisobutyronitrile) is used. The catalyst is preferably employed in an amount of about 0.05 gram-mole per one gram-equivalent of available - SH groups of the polythiol.

The reaction may be carried out at any suitable temperature, e.g., about 20°-25° C., and any suitable pressure, e.g., 760 mm Hg, for any suitable period, e.g., from about 0.5 to about 20 hours or more. Although the time required for completion of the reaction is dependent upon the particular reactants and concentrations thereof, catalyst and concentration thereof, solvent, temperature, and pressure employed, the reaction will, in general, be substantially complete within about 1 to about 10 hours.

Advantageously, the reaction is carried out with stirring and under an inert gaseous blanket, i.e., at least substantially inert to the reactants, catalyst, solvent and products employed. Nitrogen is the preferred inert gaseous blanket.

The polythiols for use in the above thiol-alkene reaction can be prepared from pentaerythritol or appropriate 1,1,1-trimethylolalkanes and appropriate mercaptoalkanoic acids by well known methods such as the general method set forth in Homberg, U.S. Pat. No. 3,144,422. The alkenes for use in such reaction can be prepared by esterification of appropriate $C_2$-$C_{15}$ alkenoyl acid halides containing terminal ene functionality, e.g., acrylic acid chloride, with appropriate 4-hydroxy-(mono- or di-alkyl)phenyl alkanol. The starting 4-(3-hydroxypropyl)-(mono- or di-alkyl)phenols used in the present invention are well known compounds which can be prepared from phenol or suitably substituted phenols by well known procedures.

The polythiol-alkene reaction set forth above can be (and preferably is) used to prepared those polyol AB compounds of this invention where n in Formula II above is 2 to 14. However, where n is 1, this reaction is inapplicable.

The compounds of the present invention are useful as stabilizers of organic materials normally subject to oxidative deterioration. Such organic materials include, for example: synthetic organic polymeric substances such as vinyl resins formed from the polymerization of vinyl halides or from the copolymerization of vinyl halides with unsaturated polymerizable compounds, e.g., vinyl esters, alpha-beta-unsaturated aldehydes and unsaturated hydrocarbons such as butadienes and styrene; poly-alpha-olefins such as polyethylene (e.g., linear low density polyethylene), polypropylene, polybutylene (e.g., polybutene-1), polyisoprene, and the like, including copolymers of poly- alpha-olefins, polyurethanes, polyamides such as polyhexamethylene adipamide and polycaprolactam; polyesters such as polymethylene terephthalates; polycarbonates, polyacetals; polystyrene; polyethyleneoxide; and copolymers such as those of high impact polystyrene containing copolymers of butadiene and styrene and those formed by the copolymerization of acrylonitrile, butadiene and/or styrene. Other materials which can be stabilized by the active compounds of the present invention include lubrication oil of the aliphatic ester type, i.e., di(2-ethylhexyl)-azelate, pentaerythritol tetracaproate, and the like; animal and vegetable derived oils, e.g., linseed oil, fat, tallow, lard, peanut oil, cod liver oil, castor oil, palm oil, corn oil, cotton-seed oil, and the like; hydrocarbon materials such as gasoline, mineral oil, fuel oil, drying oil, cutting fluids, waxes, resins and the like, fatty acids, soaps and the like.

The compounds of this invention (represented by Formula I above) may be employed in any stabilizing amount as stabilizers for organic materials normally susceptible to oxidative degradation. Such amount may be for example, from about 0.005% to about 10% by weight of the stabilized composition. For polyolefins, e.g., linear low density polyethylene, polypropylene and poly(butene-1), such amount is preferably from about 0.05% to about 5% and more preferably from about 0.1% to about 1%.

The compounds of this invention may be used alone or in combination with other stabilizers or additive materials, such as dilauryl-beta-thiodipropionate and distearyl-beta-thiodipropionate.

Other antioxidants, antiozonants, thermal stabilizers, ultraviolet light absorbers, coloring materials, dyes, pigments, metal chelating agents, etc. may also be used in the compositions of the invention.

Phosphite esters may also be used in stabilized compositions containing the novel antioxidant compounds of the present invention. Such phosphite esters include dialkyl phosphites (for example, distearyl phosphite, dilauryl phosphite, and the like, e.g., trialkyl phosphites (for example, trilauryl phosphite, tris(ethylhexyl) phosphite, and the like); and tris(alkaryl) phosphites (for example tris(nonylphenyl)phosphites, and the like).

The compounds of this invention are especially useful for stabilizing polymeric materials such as polyolefins and the like, e.g., polyethylene (especially linear low density polyethylene, i.e., LLDPE), polypropylene, poly(butene-1), and the like.

Stabilized compositions of matter of this invention may be prepared by incorporating the compounds into the organic material to be stabilized using well known methods for incorporating stabilizers into such material. For example, in general, the stabilizer may simply be physically admixed with the organic material.

It is well known that upon processing polyethylenes at elevated temperature, cross-linking takes place. This results in an apparent increase in molecular weight and hence lower melt index values. More importantly, it also results in a change in molecular weight distribution by increasing, due to cross-linking, the high molecular weight tail. In many applications, it is desired that polyethylene not cross-link while being processed. Accordingly, a feature of a good stabilizer is that the melt index does not appreciably decrease when working a polyethylene as in extrusion operations.

In contrast to polyethylenes, polypropylene typically undergoes chain scission during processing thereof at elevated temperatures, i.e. a reduction in apparent molecular weight. This is reflected typically in melt flow rate values which increase as the molecular weight decreases.

Practice of the present invention is illustrated by the following non-limiting examples. All parts, percents and other amounts given throughout this disclosure, including the examples which follow, are by weight unless otherwise indicated.

EXAMPLE 1

Pentaerythritol tetrakis [3,5-di-tert-butyl-4-hydroxphenyl-(3-propyl)oxycarbonylethylthiopropionate]

To solution of 5.28 g (0.02M) of 4-hydroxypropyl 2,6-di-tert-butylphenol and 2.02 g of triethylamine in 150 ml of toluene, was slowly added 1.81 g (0.02M) of acryloyl chloride in 20 ml of toluene with rapid stirring at room temperature. After 2 hr, the reaction mixture was filtered and concentrated in vacuo to leave a yellow liquid in quantitive yield. The 3'-(3,5-di-tert-butyl-4-hydroxyphenyl)propyl acrylate obtained was pure enough as indicated by IR, $^1$H and $^{13}$CNMR techniques.

3'-(3,5-di-tert-butyl-4-hydroxyphenyl)propyl acrylate (15.9 g, 0.05M), was added to a mixture of pentaerythritol tetra (3-mercapto-propionate) (6.1 g, 0.012M), and sodium methoxide (0.3 g). The mixture was vigorously stirred at room temperature for about 12 hr. The resulting thick gummy mixture was dissolved in toluene and washed successively with 5% HCl, saturated NaHCO₃, and saturated NaCl solutions. After drying over anhydrous MgSO₄, the solvent was removed in vacuum to leave a yellow oil in about 90% yield. The product, was identified as pentaerythritol tetrakis[3,5-di-tert-butyl-4-hydroxyphenyl-(3-propyl)oxycarbonylethylthiopropionate] on the basis of IR, $^1$H, and $^{13}$CNMR techniques. The resulting product may be hereinafter referred to as Compound A.

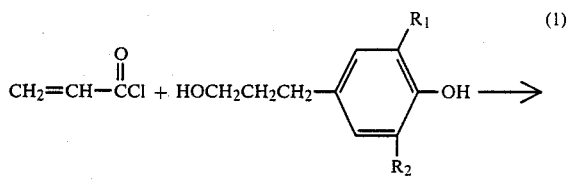

(1)

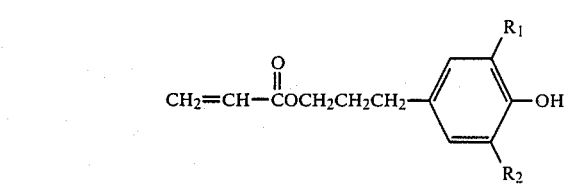

(2)

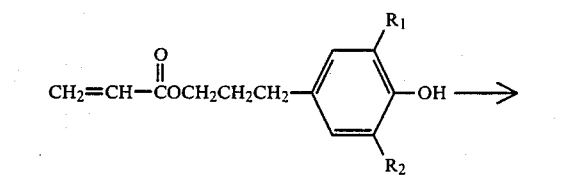

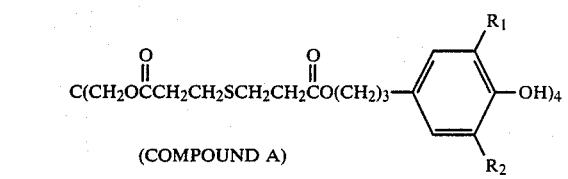

(COMPOUND A)

EXAMPLE 2

1,1,1-Trimethylolethane tris [3,5-di-tert-butyl-4-hydroxyphenyl(3-propyl)oxycarbonylethylthiopropionate]

Sodium methoxide (0.2 g), was added in one portion to a well stirred mixture of 3'-(3,5-di-tert-butyl- 4-hydroxyphenyl) propyl acrylate (13 g, 0.04M) and trimethylolethane tri(3-mercaptopropionate) (5.23 g, 0.014M) [Evans Chemetics, Darien, Ct.]. The mixture was allowed to stir overnight at ambient temperature. The resulting thick mixture was dissolved in toluene and washed with 5% HCl, sat. NaHCO₃, and sat. NaCl, respectively. The solvent was removed in vacuo after drying to leave the product, trimethylolethane tris[3,5-di-tert-butyl-4-hydroxyphenyl(3-propyl)oxycarbonylethylthiopropionate]as a yellow oil in about 90% yield. The structure of this product was confirmed on the basis of IR, $^1$H and $^{13}$CNMR spectroscopic techniques. The resulting product may be hereinafter referred to as Compound B.

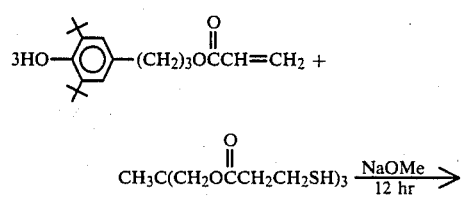

-continued

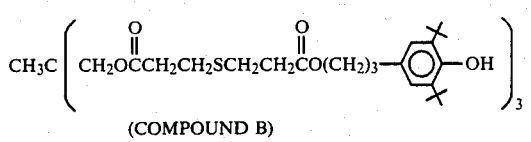

(COMPOUND B)

EXAMPLE 3

Evaluation Results in Polybutylene (P-B)

Obtained from Shell Chemical Company, Houston, Tex. a sample of unstabilized polybutylene (P-B) BR-200 having a melt index (ASTM D1238 condition E) 0.4 g/10 minutes and a density (ASTM D1505) 0.90 g/cm$^3$.

200 g of P-B BR-200 was placed on a preheated (132° C., 270° F.) 2 roll mill. The material was allowed to remain on the still rolls for 30 seconds. The mill was then turned on converting the P-B to a uniform melt. The material was removed from the 2 roll mill in a form of a sheet after exactly 3 minutes. The sheet was cooled cut into strips and pelletized.

This procedure was repeated several times except that once the P-B BR-200 was converted into a uniform melt, 2.5 g of antioxidant to be evaluated (Compound A, Compound B, etc.) was sprinkled on top of the melt. Continued rolling on the mill brought about a uniform distribution of the antioxidant within the molten resin.

The weight of each pellitized compound was determined and the pellets were mixed with an additional amount of P-B BR-200 so as to bring the final antioxidant concentration to 0.25 grams per 100 g of P-B BR-200. The blank pellets, not containing an antioxidant additive, were mixed with about 800 g of fresh P-B BR-200.

Each mixture was then extruded on a Brabender extruder at 40 rpm and the following temperature schedule. The first pass all four zones on the extruder were set at 150° C. The extruded rod was water quenched, dried and pelletized. The pellets were passed through the extruder for the second time with the temperature set at 175° C. The above procedure was followed except that in passes 3 through six the temperature was set at 200° C. In a final seventh pass the temperature was set at 250° C. Samples were retained after each pass to determine melt index. The following results were obtained:

| Compound | Melt Index g/10 min ASTMD1238E | | | |
|---|---|---|---|---|
| | Pass #1 at 200° C. | Pass #3 at 200° C. | Pass #4 at 200° C. | Pass #5 at 250° C. |
| Blank (Unstabilized) | 0.94 | 1.56 | 1.96 | 2.67 |
| Irganox 1076 (a commercial antioxidant) | 0.51 | 0.62 | 0.69 | 0.97 |
| Compound A | 0.47 | 0.55 | 0.56 | 0.80 |

| Compound | Melt Index g/10 min ASTMD1238E | | | |
|---|---|---|---|---|
| | Pass #1 at 200° C. | Pass #3 at 200° C. | Pass #4 at 200° C. | Pass #5 at 250° C. |
| Compound B | 0.53 | 0.57 | 0.65 | 0.80 |

EXAMPLE 4

Evaluation Results in Polypropylene

Polypropylene Profax 6501 was obtained from Himont, Inc. Wilmington, Del. This resin is considered to be substantially free of any antioxidant.

Seven hundred g of polypropylene resin was blended with 0.7 g calcium stearate and 0.7 g antioxidant in the Ronson blender. The dry blend was then extruded twice on a ¾" Brobender extruder at 170° C. and 50 rpm. The extruded rods were water quenched, dried and pelletized following each extrusion. The pellets were then extruded 4 times at 260° C. Pellet samples were obtained following cash extrusion to determine melt flow rate according to ASTM D1238 condition L. Pellet samples were also compression molded at 170° C. into plaques of 35 mil thickness. Yellowness index was determined on these plaques according to ASTM D1925. In this test, the higher the yellowness index value the more yellow the sample. The following results were obtained:

| ANTIOXIDANT | Melt Flow Rate ASTM D1238 Condition L (g./10 min.) | | | | Yellow Index ASTM D1925 Hunter Lab SC500 Spectrophotometer | | |
|---|---|---|---|---|---|---|---|
| | Pass #1 at 260° C. | Pass #2 at 260° C. | Pass #3 at 260° C. | Pass #4 at 260° C. | Pass #1 | Pass #3 | Pass #4 |
| Blank | 10.2 | 15.7 | 23.7 | — | 7.97 | 12.05 | — |
| Compound A | 3.4 | 5.0 | 7.7 | 10.6 | 5.86 | 8.33 | 9.50 |

EXAMPLE 5

Evaluation Results in Linear Low Density Polyethylene (LLDPE)

The LLDPE employed in our evaluation was the precursor to Union Carbide G-Resin 7047 Natural 7 antioxidant modified linear low density polyethylene resin, i.e. such resin prior to incorporating an antioxidant. This copolymer typically has a density of 0.92, a melt index of about 1.0 (ASTM D1238 condition E) and 1-butene comonomer content of about 3–5 mole percent.

A dry blend was prepared by admixing at room temperature 1.0 g of the antioxidant and 200 g of resin in a Ronson blender. The blender was operating at speed 10 for 3 minutes. The concentrate was transferred to a polyethylene bag and additional 800 g of resin added and blended in the bag.

The blend was then extruded on a ¾" Brabender extruder at 50 rpm with all 4 zones set at 210° C. The extruded rod was water quenched, dried and pelletized. The procedure was repeated five times at 50 rpm and 260° C. Pellet samples were retained following each extrusion to determine melt index. The same procedure was repeated on LLDPE resin not containing an antioxidant.

The following results were obtained:

| Compound | Melt Flow Index, ASTM D1238 E (g./10 min.) | | |
|---|---|---|---|
| | Pass #1 at 260° C. | Pass #3 at 260° C. | Pass #5 at 260° C. |
| Blank (Unstabilized) | 0.61 | 0.38 | 0.29 |
| Compound A | 0.91 | 0.82 | 0.73 |

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A polyol carboxyalkylthioalkanoesterphenol compound having the following Formula I:

where Y is a monovalent group having the following Formula II

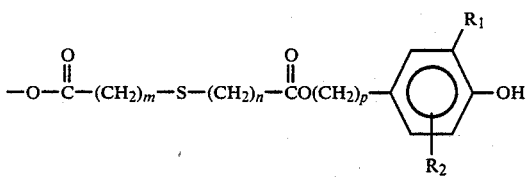

where $R_1$ is an alkyl group containing from one to eight carbon atoms or a cycloalkyl group containing from five to twelve carbon atoms; $R_2$ is hydrogen, an alkyl group containing from one to eight carbon atoms or a cycloalkyl group containing from five to twelve carbon atom; m is a selected integer from 1 to about 10, and n is a selected integer from 1 to about 14, p is a selected integer from 1 to about 8; and Z is $-CH_2Y$ or an alkyl group containing from 1 to about 8 carbon atoms; and X is Y or $-OH$.

2. The compound is claim 1 wherein $R_1$ and and $R_2$ are tertiary alkyl groups.

3. The compound of claim 1 wherein $R_1$ and $R_2$ are tertiary butyl groups.

4. The compound of claim 1: Pentaerythritol tetrakis [3,5-di-tert-butyl-4-hydroxyphenyl-(3-propyl) oxycarbonylethylthiopropionate].

5. The compound of claim 1: 1,1,1-trimethylolethane tris[3,5-di-tert-butyl-4--hydroxyphenyl-(3-propyl)oxycarbonylethylthiopropionate].

6. A composition of matter comprising an organic material normally subject to oxidative deterioration and a stabilizing amount of the compound of claim 1.

7. The compound of claim 6 wherein the organic material is a polymeric material.

8. The composition of claim 7 wherein the polymeric material is a polyolefin.

9. The composition of claim 8 wherein the polyolefin is linear low density polyethylene.

10. The composition of claim 8 wherein the polymeric material is polypropylene.

11. The composition of claim 8 wherein the polymeric material is polybutylene.

12. A composition of matter comprising an organic material normally subject to oxidative deterioration and a stabilizing amount of the compound of claim 2.

13. A composition of matter comprising an organic material normally subject to oxidative deterioration and a stabilizing amount of the compound of claim 3.

14. A composition of matter comprising an organic material normally subject to oxidative deterioration and a stabilizing amount of the compound of claim 4.

15. A composition of matter comprising an organic material normally subject to oxidative deterioration and a stabilizing amount of the compound of claim 5.

16. A composition of matter comprising an organic polymeric material normally subject to oxidative deterioration and a stabilizing amount of the compound of claim 4.

17. A composition of matter comprising an organic polymeric material normally subject to oxidative deterioration and a stabilizing amount of the compound of claim 5.

* * * * *